US011977998B2

(12) United States Patent
Stiller et al.

(10) Patent No.: US 11,977,998 B2
(45) Date of Patent: May 7, 2024

(54) SURGICAL WORKFLOW SUPPORT SYSTEM

(71) Applicant: Storz Endoskop Produktions GmbH, Tuttlingen (DE)

(72) Inventors: Heinz-Werner Stiller, Beringen (CH); Matteo Contolini, Santa Barbara, CA (US)

(73) Assignee: STORZ ENDOSKOP PRODUKTIONS GMBH, Tuttlingen (DE)

( * ) Notice: Subject to any disclaimer, the term of this patent is extended or adjusted under 35 U.S.C. 154(b) by 1055 days.

(21) Appl. No.: 14/279,015

(22) Filed: May 15, 2014

(65) Prior Publication Data

US 2015/0332196 A1 Nov. 19, 2015

(51) Int. Cl.
| | |
|---|---|
| *G06Q 10/0631* | (2023.01) |
| *G16H 20/40* | (2018.01) |
| *G16H 40/20* | (2018.01) |
| *G16H 40/63* | (2018.01) |
| G16H 50/20 | (2018.01) |
| G16H 70/20 | (2018.01) |

(52) U.S. Cl.
CPC ....... *G06Q 10/06316* (2013.01); *G16H 20/40* (2018.01); *G16H 40/20* (2018.01); *G16H 40/63* (2018.01); *G16H 50/20* (2018.01); *G16H 70/20* (2018.01)

(58) Field of Classification Search
CPC .............. G06Q 10/06316; G06Q 50/22; G06F 19/3481; G06F 19/345; G06F 19/327; G06F 19/3406; G16H 20/30; G16H 20/40; G16H 20/70; G16H 20/90
See application file for complete search history.

(56) References Cited

U.S. PATENT DOCUMENTS

| | | |
|---|---|---|
| 5,692,125 A | 11/1997 | Schloss et al. |
| 6,714,913 B2 | 3/2004 | Brandt et al. |
| 7,274,290 B2 | 9/2007 | Morita et al. |
| 7,310,607 B2 | 12/2007 | Brandt et al. |
| 7,371,068 B2 | 5/2008 | Lloyd et al. |
| 7,443,303 B2 | 10/2008 | Spear et al. |

(Continued)

FOREIGN PATENT DOCUMENTS

| | | |
|---|---|---|
| WO | 2008147567 A1 | 12/2008 |
| WO | 2011060185 A1 | 5/2011 |

(Continued)

OTHER PUBLICATIONS

R. H. Taylor and D. Stoianovici, "Medical robotics in computer-integrated surgery," in IEEE Transactions on Robotics and Automation, vol. 19, No. 5, pp. 765-781, Oct. 2003, doi: 10.1109/TRA.2003.817058. (Year: 2003).*

(Continued)

*Primary Examiner* — Rachel L. Porter

(74) *Attorney, Agent, or Firm* — Honigman LLP

(57) ABSTRACT

Methods and systems for controlling a workflow in an operating room including interconnected medical devices that support surgical systems and surgical operations. Methods and systems to control clinical information through the use of a medical device, such that use of a medical device at least partially determines the clinical information that is displayed on a display monitor.

42 Claims, 7 Drawing Sheets

(56) References Cited

U.S. PATENT DOCUMENTS

| | | |
|---|---|---|
| 7,447,644 B2 | 11/2008 | Brandt et al. |
| 7,533,353 B2 | 5/2009 | Dvorak et al. |
| 8,313,432 B2 | 11/2012 | Chiu et al. |
| 8,355,928 B2 | 1/2013 | Spahn |
| 8,411,034 B2 | 4/2013 | Boillot et al. |
| 2005/0001024 A1* | 1/2005 | Kusaka ............... G06V 40/16 340/5.2 |
| 2005/0128184 A1* | 6/2005 | McGreevy ......... A61B 18/1206 345/156 |
| 2006/0282302 A1 | 12/2006 | Hussain |
| 2007/0118400 A1 | 5/2007 | Morita et al. |
| 2007/0136218 A1 | 6/2007 | Bauer et al. |
| 2008/0083414 A1* | 4/2008 | Messerges .......... A61B 5/0205 600/301 |
| 2008/0086035 A1 | 4/2008 | Messerges et al. |
| 2008/0104547 A1 | 5/2008 | Morita et al. |
| 2008/0114212 A1 | 5/2008 | Messerges |
| 2008/0114214 A1 | 5/2008 | Messerges |
| 2008/0114226 A1 | 5/2008 | Music et al. |
| 2008/0164998 A1 | 7/2008 | Scherpbier et al. |
| 2008/0198223 A1* | 8/2008 | Iriyama ............. A61B 1/00011 348/E7.085 |
| 2008/0253519 A1 | 10/2008 | Bonfiglio et al. |
| 2009/0021475 A1 | 1/2009 | Steinle et al. |
| 2009/0125840 A1* | 5/2009 | Squilla ................. G16H 40/20 715/810 |
| 2009/0182577 A1* | 7/2009 | Squilla ................. G06Q 10/06 705/2 |
| 2010/0022849 A1 | 1/2010 | Franz et al. |
| 2011/0157480 A1* | 6/2011 | Curl .................... G16H 40/67 348/739 |
| 2012/0229383 A1 | 9/2012 | Hamilton et al. |
| 2013/0046280 A1* | 2/2013 | Martin ................. G16H 20/13 604/503 |
| 2013/0046291 A1* | 2/2013 | Palmer ............. A61B 17/00234 606/1 |
| 2013/0179162 A1 | 7/2013 | Merschon et al. |
| 2013/0204428 A1 | 8/2013 | Steinle et al. |
| 2013/0225999 A1 | 8/2013 | Banjanin et al. |
| 2014/0006049 A1 | 1/2014 | Moctezuma de la Barrera |
| 2014/0184770 A1* | 7/2014 | King .................. A61B 1/00114 348/75 |
| 2014/0204190 A1* | 7/2014 | Rosenblatt, III ......... G09B 5/00 348/77 |
| 2014/0276056 A1* | 9/2014 | Ohta ................... A61B 8/565 600/407 |
| 2017/0202443 A1* | 7/2017 | Mihalca ............. G02B 23/2469 |
| 2021/0153960 A1* | 5/2021 | Griffiths ................ A61B 50/10 |

FOREIGN PATENT DOCUMENTS

| | | |
|---|---|---|
| WO | 2011060187 A1 | 5/2011 |
| WO | 2012044334 A2 | 4/2012 |
| WO | 2012129669 A1 | 10/2012 |
| WO | 2013038293 A1 | 3/2013 |

OTHER PUBLICATIONS

Ext. European Search Report Application No. 15167063.5 Completed: Nov. 9, 2016; dated Nov. 17, 2016 10 Pages.

Florent Lalys et al., Automatic knowledge-based recognition of low-level tasks in ophthalmological procedures, International Journal of Computer Assisted Radiology and Surgery, 2013, 8 (1), pp. 39-49 (2 page abstract).

N. Padoy et al., Statistical Modeling and Recognition of Surgical Workflow Medical/Image Analysis (2010), vol. 16, Issue 3, Apr. 2012 (published online Dec. 2010), pp. 632-641.

Houliston BR et al.(2011) TADAA: towards automated detection of anesthetic activity, Methods Inf Med 50(5): 464-471; (1 page abstract).

European Office Action Application No. 15167063.5 Completed: Nov. 27, 2017 5 pages.

* cited by examiner

SURGICAL WORKFLOW SUPPORT SYSTEM

FIELD OF THE INVENTION

The invention generally relates to interconnected medical devices and information systems that support surgical systems and surgical operations.

BACKGROUND OF THE INVENTION

Modern Integrated Operating Rooms ("IOR") consist of interconnected medical devices and information systems. The typical IOR is a cluttered environment that is constituted of a myriad of medical devices, surgical instruments, monitors, touch screens, input devices (e.g. footswitches, computer keyboards and mouse, camera head buttons, etc.), communication systems, and so on. One reason for such clutter is that a multitude of equivalent input/output devices are needed by the surgical team to manage the flow of information and to control the different devices in the IOR. For example, multiple LCD displays are typically needed in the surgical field to view, patient information (e.g., X-Rays, CT scans, MRI scans, vital signs, etc.), to display the surgical image and to control the IOR (e.g., using an IOR touchscreen or by voice and/or gesture control). Furthermore, it is not uncommon for a surgeon to have to operate an array of several footswitches, each triggering individual functions on different devices in the IOR.

It is a disadvantage of current IOR systems that the IOR is cluttered, and the user (e.g. a surgeon) is overloaded with information, as the user cannot dedicate his or her mind 100% to a surgery at hand because the user is distracted by other tasks (e.g., which footswitch is required to press to take an image of the patient). Existing workflow management systems include U.S. Pat. No. 8,355,928 to Spahn; U.S. Patent Publication No. 2009/0125840 to Squilla et al.; U.S. Patent Publication No. 2010/0022849 to Franz et al.; U.S. Patent Publication No. 2008/0114214 to Messerges; U.S. Patent Publication No. 2008/0114212 to Messerges; Florent Lalys et al., Automatic knowledge-based recognition of low-level tasks in ophthalmological procedures, International Journal of Computer Assisted Radiology and Surgery, 2013, 8 (1), pp. 39-49; Houliston B R et al. (2011) TADAA: towards automated detection of anesthetic activity, Methods Inf Med 50(5): 464-471; N. Padoy et al., Statistical Modeling and Recognition of Surgical Workflow Medical/Image Analysis (2010), Volume 16, Issue 3, April 2012 (published online December 2010), pp. 632-641.

None of the existing systems, however, adequately reduces IOR clutter, so that a user, such as a surgeon, is only provided with the required information for the specific task at hand, so that the workflow of a surgery is optimized, and so that the user can concentrate fully on the specific task at hand, rather than being overloaded with extraneous information.

Thus, there exists a need to provide a method and system that is able to support the workflow of a surgery and that optimizes and improves the workflow of a medical procedure.

SUMMARY OF THE INVENTION

To improve upon the prior art, it is an object of the present invention to provide a workflow support system that is able to automatically detect and identify individual surgical phases and/or tasks, and to correlate relevant information to a display to optimize and improve the workflow of a medical procedure.

Another object of the invention is to provide a system that is able to automatically navigate the workflow in an IOR to optimize the various settings that are required for each phase or task in a medical procedure.

These and other objects of the invention are achieved by providing a system for managing workflow of a medical procedure, the system comprising: a processor; a database storing clinical information; at least one display monitor able to display the clinical information; software executing on said processor for displaying a subset of the clinical information on said at least one display monitor; and at least one medical device, the at least one medical device used in the medical procedure, such that during the medical procedure, use of the at least one medical device at least partially determines the subset of clinical information that is displayed on the at least one display monitor.

In certain embodiments, use of the at least one medical device determines all of the subset of clinical information that is displayed on the at least one display monitor. In certain embodiments, the software is stored on a memory, a computer readable medium or a non-transitory medium.

In certain embodiments, the medical procedure is performed in an operating room. In certain embodiments, the medical procedure is a set of surgeries, such as a transplant surgery. In certain embodiments, the processor is stored within a computer or a server. In certain embodiments, the system includes a graphical user interface on the at least one display for displaying the subset of the clinical information on said at least one display monitor. In certain embodiments, the graphical user interface comprises at least one dashboard for displaying the clinical information on the display.

In certain embodiments, the clinical information comprises patient data. In certain embodiments, the clinical information comprises medical data that is relevant to performing a medical or surgical procedure. Such medical data may include, but is not limited to, a patient's heart rate, blood pressure, sugar levels, and other such data that is important to monitor during a medical procedure.

In certain embodiments, the medical data is displayed in the form of graphs and charts to present the most relevant data during the medical procedure.

In certain embodiments, a different subset of the clinical information is displayed on the at least one display monitor for each stage of a multi-stage medical procedure. In certain embodiments, a relevant subset of the clinical information is displayed on the at least one display monitor for each stage of a multi-stage medical procedure. The relevant subset of the clinical information is the subset that is most directly relevant to the particular stage of the medical procedure. In certain embodiments, the subset of data includes various data parameters, and only relevant data parameters are displayed on the display during particular stages of the surgery, as other data that is not relevant is not displayed, thus, reducing the amount of information displayed. In certain embodiments, the subset of data displayed varies depending upon the intended user of the at least one medical device, such that subset of data is dynamic and different subsets of data can be displayed depending upon the user and/or the level of the user of the at least one medical device.

In certain embodiments, the at least one medical device includes at least one control, wherein the at least one control performs a different task during different stages of the multi-stage medical procedure. In certain embodiments, the at least one control can be an electronic control, such as a control on a touchscreen. In certain embodiments, the control can be a manual control such as a button, a switch, or another such manual element than can be actuated or toggled between positions and that can be adjusted by a user either manually or automatically. In certain embodiments, the control can be an audio input device, such that voice commands can control the medical device. In certain embodiments, the control can be a motion detector, such that various gestures can control the medical device.

In certain embodiments, the at least one control is able to be reprogrammed to perform a different task during different stages of the multi-stage medical procedure. In certain embodiments, the at least one control has more than one function, such that the at least one control is able to perform a different task during different stages of the multi-stage medical procedure. In certain embodiments, the at least one control can be reprogrammed and is dynamic so that the control performs the most appropriate actions for the particular surgical step of the surgical procedure.

In other embodiments, the at least one control can be reprogrammed based upon the specific type of procedure. For example, if the procedure is a colonoscopy, a control on an endoscope will have a different function than if the procedure were a prostatectomy. In other embodiments, the control can be reprogrammed manually, automatically or via a third party user.

In certain embodiments, the control is able to be visually adjusted, such that the user is able to determine the status of the control during a specific procedure to determine the function of the control. For example a control might be lit up to a certain color during a particular procedure to indicate that it has a certain function, while it may have a different color during a different medical procedure or during a different step or stage of the medical procedure. In certain embodiments, other methods and systems of visually adjusting the control are possible, such as having the control flash on and off, so as to indicate that the control has a certain function during a particular procedure.

In certain embodiments, the control is able to perform a different task during different stages of a procedure. For example, the control might be first used for intubation, and may then be used to actuate a cutting mechanism as in an endoscopic tool or instrument. This is advantageous, as having a fewer amount of controls leads to a decrease in the number of control devices in an operating room.

In certain embodiments, the at least one medical device is connected to the processor, and such that movement or use of the at least one medical device controls the subset of clinical information that is displayed on the at least one display monitor, as the processor communicates with the display to provide the appropriate information on the display. For example, if an endoscope is picked up, than a certain subset of information is displayed on the display. In certain embodiments, there is software executing on the processor, such that the software contains computer programs and controls that allow the processor to communicate with the display to provide the appropriate information on the display. In certain embodiments, the software is stored on a memory or a computer readable medium.

In certain embodiments, use of the at least one control on the at least one medical device controls the subset of clinical information that is displayed on the at least one display monitor. For example, if the button triggering the white-balance function on an endoscope is actuated, than it can be deducted that the endoscope is about to be inserted into the body, and a certain subset of information is displayed on the display. In other examples, if a button activates a certain surgical functionality, the software identifies such activation as a surgical step (or as a transition into a surgical phase) which in turn triggers the display of a different subset of information on the display. Accordingly, the control is able to control the subset of the display based upon the use of the button or the use of the at least one medical device.

In certain embodiments, the at least one medical device includes a sensor, an RFID tag, or a type of active or passive identifier that interacts with the processor. Active identifiers can be, for example, other type of radio-based identification tags, or one or more LEDs flashing a certain light pattern. Passive identifiers can be barcodes or QR codes that can be read by a camera. In certain embodiments, the at least one medical device includes an accelerometer within the at least one medical device to detect movement of the at least one medical device. In certain embodiments, the at least one medical device sends signals to interact with the processor.

In certain embodiments, the steps of the medical procedure are controlled at least in part by the at least one medical device. In certain embodiments, by using or moving the at least one medical device, the processor is able to determine the step or stage of the medical procedure, simply through the use and/or actuation of the at least one medical device. In this manner, the system recognizes the step of the procedure, and relevant information for a particular stage of the procedure is provided to a user. In certain embodiments, the medical procedure is a surgery or surgical procedure. In certain embodiments, the medical procedure involves a set of surgeries that are performed at the same time. For example, an organ may transplanted from a donor to a recipient during the set of surgeries. In certain embodiments, at least one medical device may be used in each of the surgeries, such that each of the at least one medical devices controls the data displayed on the at least one display in each of the surgeries. In certain embodiments, the surgeries occur in different locations, such as different hospital rooms or even different hospitals. In certain embodiments, the system includes more than one processor, such that the system for each surgery is connected to one another, so that the progress of the surgeries are monitored and information for each of the surgeries is available to each of the sets of individuals performing the respective surgeries.

In certain embodiments, the processor is able to sort through contextual information such as the type of procedure being performed, and can determine the step or stage of the medical procedure, simply through the use of the at least one medical device. The type of medical procedure is known a priori, either because a nurse manually types it into the system, or because it is loaded automatically from the hospital information system (e.g., DICOM, HL7). Since the type of procedure is known, and if for example a certain type of scalpel is expected to be used for initial incision in this type of medical procedure, then when movement of the scalpel is detected, the processor determines that the surgical phase has reached the step of initial incision.

In certain embodiments, the processor receives signals from the at least one medical device to determine the step or stage of the medical procedure. In certain embodiments, the signals may be electronic signals such as video signals. In certain embodiments, the electronic signals can be provided by a third device, such as a room camera (video signals) or radio receiver (e.g., RFID signal).

In certain embodiments, the processor is able to sort through patient information, vital sign data, state of medical devices, input from surgeons and nurses (on the control user interface (UI) and on other devices/medical systems), and all the preceding procedural steps that have been identified so far (state within the workflow), even individual preferences/ profiles of the surgical team. Such contextual information can be referred to as the "IOR state." After sorting through this information, the processor is able to determine the step or stage of the medical procedure.

In certain embodiments, the system includes a machine learning module. In certain embodiments, the machine learning module includes rules, such that the rules in the machine learning module adjust the steps of the medical procedure based upon the use of the at least one medical device during the medical procedure.

For example, if the steps of the surgical procedure require certain steps and the surgeon picks up an instrument that is typically not required in the procedure, then the machine learning module will store the deviating event together with the full IOR state at that time.

In certain embodiments, the rules have an associated risk level, so that rules having a high risk level are not automatically updated by the system.

In certain embodiments, the risk level is expressed as a continuum between a minimum and a maximum value, so that rules with progressively higher risk level are only updated after a progressively larger set of usage data showing a consistent usage pattern is collected. In this manner, the system is intelligent and updates according to the usage pattern and level of risk. In certain embodiments, the risk is determined by a surgeon on a scale of one to ten.

In certain embodiments, the machine learning module includes both software elements and/or hardware elements. In certain embodiments, the machine learning module includes instructions that execute on a memory or on a processor. In certain embodiments, the machine learning module is stored on a memory or a computer readable medium.

In certain embodiments, the system includes an image recognition module. In certain embodiments, the image recognition module performs an analysis of signals provided by the at least one medical device and at least partially uses image recognition algorithms to identify features in the signals provided by the at least one medical device. In certain embodiments, the image recognition module includes both software elements and/or hardware elements. In certain embodiments, the image recognition module includes instructions that execute on a memory or on a processor. In certain embodiments, the image recognition module is stored on a memory or a computer readable medium.

In certain embodiments, the image recognition module and the machine learning module are part of the same system and method and are not mutually exclusive of one another. In other embodiments, the image recognition module and the machine learning module are not part of the same system and method and are mutually exclusive of one another.

In certain embodiments, the at least one medical device is a camera or more than one camera. In certain embodiments, the signals are video signals. In certain embodiments, the signals are data provided by the at least one medical device.

In certain embodiments, the image recognition module may identify when (and what) tools are inserted into the patient via information provided by a video feed from the at least one medical device. In certain embodiments, the at least one medical device is a room camera. In certain embodiments, the image recognition module is able to interpret data and signals provided from the room camera.

In certain embodiments, in a video feed from an endoscopic camera, the image recognition module may identify blood vessels, anatomic features, and surgical tools.

In certain embodiments, the machine learning module will periodically (either based on schedule or based on the number of events collected) evaluate its database of deviating events, determine any correlation between particular deviating events and the corresponding IOR states, and if such correlation is above a threshold, update the relevant step(s) of the medical procedure. Note that the machine learning module may determine that a particular deviating event occurs only when, for example, a certain surgeon operates on a patient within a certain age group. Then, the machine learning module will create a new workflow that is customized for the particular situation. In certain embodiments, this can be customized based upon the specific user performing the procedure. In certain embodiments, the new workflow created by the machine learning module is stored on a memory or a computer readable medium.

In certain embodiments, the system includes a user override, so that the user can manually override the steps of the medical procedure. In certain embodiments, the override is based on a voice command, on a gesture, or on an input command such as a mouse or keyboard entry.

In certain embodiments, the system automatically and adaptively learns the preferred settings for each of the stages of a surgical procedure. In certain embodiments, the system includes artificial intelligence. In certain embodiments, the artificial intelligence includes statistical methods and algorithms so that the machine learning module and workflow management system are able to learn and interact to optimize the medical procedure. In certain embodiments, the workflow management system is triggered when at least one member of the surgical team logs in into the system, or when the patient/procedure data is downloaded from a DICOM server, or based on the IOR schedule.

In certain embodiments, the system collects clinical information and uses the clinical information to identify the particular stage of a surgical procedure.

In certain embodiments, the system provides reminders to the user to improve the workflow of a medical procedure and/or to improve the safety of a patient.

In certain embodiments, the system includes various medical device parameters to at least partially determine a stage or phase of the medical procedure. In certain embodiments, the medical device parameters are control parameters. In other embodiments, the medical device parameters are signals provided to the processor.

In certain embodiments, clinical information provided by the at least one medical device is used to at least partially identify additional fine-grained steps within the medical procedure.

In certain embodiments, the at least one medical device is controlled via speech recognition and/or gesture control and/or an input device. In certain embodiments, the at least one machine learning module updates said rules after receiving commands via speech recognition and/or gesture control and/or an input device.

In certain embodiments, the image recognition module is augmented by speech recognition and/or gesture control and/or an input device. In certain embodiments, the image recognition module is able to learn the visual features of previously unseen medical devices and/or gestures.

In certain embodiments, the processor includes an override that allows a user to control the subset of clinical information that is displayed on the at least one display monitor.

In certain embodiments, the system further includes software executing on the processor that provides reminders to suggest that certain steps during the medical procedure should be taken by a user.

In certain embodiments, the system includes software executing on the processor, such that the at least one medical device provides audible warnings to a user and/or provides additional instructions to a user to suggest steps during the medical procedure.

In certain embodiments, the system further includes a second medical device, the second medical device providing a second subset of medical data, such that during the medical procedure, the use of the second medical device at least partially determines the subset of clinical information that is displayed on the at least one display monitor.

In certain embodiments, the first medical device is in communication with the second medical device.

In certain embodiments, the system further includes a third medical device, the third medical device providing a third subset of medical data. In certain embodiments, the first medical device is used on a first patient and the third medical device is used on a second patient.

In certain embodiments, the medical procedure is a transplant surgery. In certain embodiments, the medical procedure involves a set of surgeries that are performed at the same time, such that an organ is transplanted from a donor to a recipient.

In certain embodiments, the system further includes a controller, the controller being used to monitor the progress of the medical procedure.

In certain embodiments, the controller receives information from the first medical device and the third medical device, such that the controller provides relevant information to determine the progress of the medical procedure.

In certain embodiments, during the medical procedure, the controller provides the progress of the medical surgery by providing updates through the at least one display monitor.

In certain embodiments, when multiple medical devices are used, information provided by the devices is used to determine additional fine-grained steps within the particular procedure. In certain embodiments, the information provided by the devices includes parameters, settings, sensor data and/or image data.

In certain embodiments, information from the machine learning module, the image recognition module, the at least one medical device, and sensors are combined to provide additional fine-grained detection of steps in the medical procedure. Such fine-grained detection of steps include determining various steps in the medical procedure, as well as additional sub-steps or minor steps in the medical procedure that are logical oriented, such that such steps are only required if specific previous steps occur. For example, certain medical steps are only performed if previous steps are taken, such that if a patient has an organ insufflated, then the surgical procedure may involve other steps that have to do with preparing a patient before insufflation and after insufflations.

In certain embodiments, the clinical information is divided into subsets according to the role of an intended recipient of the clinical information.

In certain embodiments, the system includes at least two display monitors, wherein at least one display monitor displays a subset of information that is relevant for a first intended recipient, and wherein at least one display monitor displays a subset of information that is relevant for a second intended recipient.

Other objects of the invention are achieved by providing a method for managing workflow of a medical procedure in an operating room, the method comprising: providing a processor able to process clinical information; providing at least one display monitor able to display the clinical information; providing at least one medical device, the at least one medical device being used in the medical procedure; wherein use of the at least one medical device in the medical procedure at least partially determines a subset of the clinical information that is displayed on the at least one display monitor. In certain embodiments, use of the at least one medical device determines all of the subset of clinical information that is displayed on the at least one display monitor In certain embodiments, the medical procedure is performed in an operating room. In certain embodiments, the processor is stored within a computer or a server. In certain embodiments, the at least one display includes a graphical user interface for displaying the subset of the clinical information on said at least one display monitor. In certain embodiments, the graphical user interface comprises at least one dashboard for displaying the clinical information on the display.

In certain embodiments, the clinical information displayed on the at least one display monitor is for a multi-stage medical procedure.

In certain embodiments, the at least one medical device includes at least one control, wherein the at least one control performs different tasks during different stages of the multi-stage medical procedure. In certain embodiments, the at least one control can be an electronic control, such as a control on a touchscreen. In certain embodiments, the control can be a manual control such as a button, a switch, or another such manual element than can be actuated or toggled between positions.

In certain embodiments, the identified stage of the medical procedure to be performed determines the data displayed on the at least one display monitor.

In certain embodiments, the at least one medical device includes a sensor, an RFID tag, or a type of active or passive identifier that interacts with the computer. In certain embodiments, the at least one medical device includes an accelerometer to detect movement of the at least one medical device.

In certain embodiments, the at least one medical device includes control parameters, wherein changes to the control parameters of the at least one medical device controls the subset of clinical information that is displayed on the at least one display monitor.

In certain embodiments, the processor includes an override that allows a user to control the data that is displayed on the at least one display monitor. In certain embodiments, the override is based upon a voice command, a gesture, or on an input command.

In certain embodiments, the at least one medical device includes an input device, such as a foot pedal. In certain embodiments, the at least one medical device is a scalpel, an endoscope or a laryngoscope. In certain embodiments, the at least one medical device is an input device that can be dynamically re-programmed. In certain embodiments, the at least one medical device is controlled via speech recognition and/or gesture control.

In certain embodiments, the method further comprises software executing on the processor that provides reminders to suggest that certain steps during the medical procedure should be taken by a user.

Other objects of the invention are achieved by providing a system for managing workflow of a medical procedure in an operating room, the system comprising a processor; a database storing clinical information; at least one display monitor able to display the clinical information; software executing on said processor for displaying a subset of the clinical information on said at least one display monitor; and an image recognition module, the image recognition module able to detect a stage of the medical procedure to at least partially determine the subset of clinical information that is displayed on the at least one display monitor. In certain embodiments, use of the at least one medical device determines all of the subset of clinical information that is displayed on the at least one display monitor.

In certain embodiments, the system includes at least one medical device, the at least one medical device used in the medical procedure able to interact either actively or passively with the image recognition module.

In certain embodiments, the at least one medical device interacts with the image recognition module via a sensor, an RFID tag, or other type of active or passive identifier.

In certain embodiments, the system includes software executing on the processor that provides reminders to suggest that certain steps during the medical procedure should be taken by a user, such as a surgeon.

In certain embodiments, the at least one medical device includes at least one control, wherein the at least one control performs a different task during different stages of the multi-stage medical procedure. In certain embodiments, the at least one control can be an electronic control, such as a control on a touchscreen. In certain embodiments, the control can be a manual control such as a button, a switch, or another such manual element than can be actuated or toggled between positions.

In certain embodiments, the at least one control is able to be reprogrammed to perform a different task during different stages of the multi-stage medical procedure.

In certain embodiments, the processor is located within a computer or server. In certain embodiments, the clinical information consists of patient data and is grouped by various patients in a database.

In certain embodiments, the at least one medical device is controlled via speech recognition and/or gesture control and/or an input device.

In certain embodiments, the image recognition module is augmented by speech recognition and/or gesture control and/or an input device.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
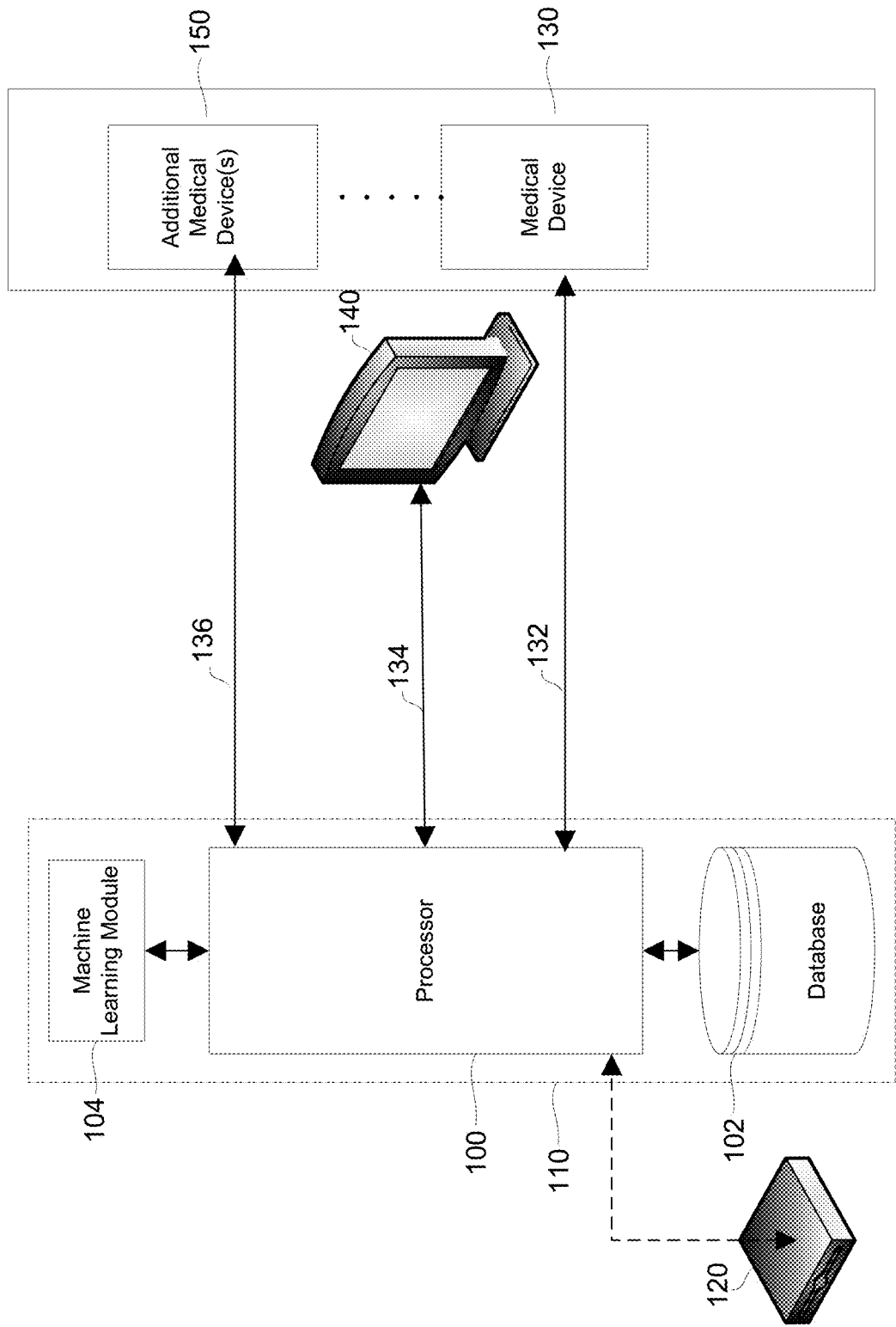
FIG. 1 is a schematic view of a surgical workflow support system of an embodiment of the present invention.

In the following description, numerous details are set forth for purpose of explanation. However, one of ordinary skill in the art will realize that the invention may be practiced without the use of these specific details. For instance, the techniques described below are described in a specified order, but other embodiments may change the order of the operations while still embodying the current invention.

The present invention provides a workflow support system that is able to identify individual surgical phases and/or tasks. The system is able to automatically navigate the workflow in an IOR to optimize the various settings that are required for each phase or task. In certain embodiments, the system only displays information that is necessary for that medical phase, and thus displays various subsets of information, the subsets of information being related to the medical phase or task. In this manner, a user (such as a surgeon), is not overwhelmed by data during specific steps in a medical operation.

As defined herein, a "subset" of clinical information is a set of clinical information that is less than the total set of clinical information stored on a computer or server. For example, a subset of clinical information may include a set of information related to a patient's blood pressure and pulse, which is a smaller set than all the clinical information of the patient that is maintained by a computer and/or server (e.g., the computer may maintain additional clinical information such as X-Rays, MRI scans, a patient's sugar levels and other such clinical information, while only displaying "subsets" of the information at a time). Various subsets of data can be displayed based upon the particular stages of a medical procedure. In this manner, only a subset of clinical information that is relevant to a step in the medical procedure is displayed and a different subset of clinical information can be displayed during a different step of the medical procedure. In certain embodiments, the same subset of information can be displayed in different steps if necessary for the medical procedure.

As defined herein "clinical information" is information that is related to a clinical or medical procedure. Clinical information includes medical data and patient data. Such medical data may include but is not limited to a patient's heart rate, blood pressure, sugar levels, and other such data that is important to monitor during a medical procedure. Clinical information may also include diagnostic medical data such as X-Rays, CT scans, MRI scans, lab results, stills and videos from past procedures, etc. Clinical information is also information that is generated by the system to aid the surgical workflow. For example, given the set of raw data obtained from different patient vital sign monitors and/or medical devices, the system may display information, or issue audible warnings, to alert the surgical team that the patient may be incurring an increased risk of going into cardiac arrest. As another example, in a hip replacement surgery, when the system detects that the old bone has been removed, it may display information directing a nurse to prepare the implant for insertion into the body. Specific, additional instructions may also be provided as to how the implant should be prepared.

In certain embodiments, clinical information also comprises information that is exchanged between connected IORs. For example, in a living-donor kidney transplant surgery, the system monitors the progress of the surgery on the donor and provides relevant information to the surgical team of the recipient so that the two surgeries can proceed in synchronous steps, and so that the recipient is ready to receive the organ when the organ has been extracted from the donor. The system may also monitor both surgeries simultaneously, so that if for example the surgical steps on the recipient incur some delaying complications, then the system may instruct the surgical team on the donor side to slow down the procedure.

In certain embodiments, clinical information is divided in subsets according to the role of the intended recipient. For example, one or more monitors in the surgical field may display a subset of information that is relevant for the surgeon, while a monitor at the nurse's station or near the instrument cart may display a subset of information that is relevant for a nurse.

Incorporated by reference into this application is U.S. patent application Ser. No. 13/949,724 entitled "Multi-Dimensional Surgical Safety Countermeasure System" filed on Jul. 24, 2013. The contents of U.S. patent application Ser. No. 13/949,724 is incorporated into this application in its entirety.

In certain embodiments of the present invention, the system involves using at least one medical device to control the information displayed in the at least one display monitor. The system is able to understand the workflow of the surgery based upon the medical device(s) being used in the surgery, and thus to control the information shown on the display during a particular phase of the surgical workflow.

In certain embodiments, the medical device can interact with a checklist so that a checklist indicates to a user to use a medical device, whereupon use of the medical device controls the information displayed in the at least one display monitor by displaying a subset of data on the display, the subset of data being relevant to the particular stage of the medical procedure.

In certain embodiments, the information on the display and the checklist is provided via a graphical user interface ("GUI") and on a dashboard on the GUI. A "dashboard" as defined herein is one or more window panes for providing information. Window panes can be provided for a specific view for one or more clinical data items. For instance, these windows might show different information for a particular patient. One window pane might show a CT scan of the patient, the other window pane might show a lab report, and the third window might show a graph of oxygen saturation.

In certain embodiments, the system provides reminders to a user to improve the workflow and/or the patient's safety during a medical operation. In certain embodiments, the system automatically and adaptively learns the preferred settings for each of the medical steps of a medical procedure. In certain embodiments, the preferred settings for each of the medical steps of a medical procedure vary depending upon the user.

Referring to FIG. 1, FIG. 1 shows an exemplary system for managing workflow of a medical procedure in an operating room. The system includes at least one processor 100. The processor 100 may be any device, system or part thereof that controls at least one operation and/or executes software applications or machine-readable instructions. The processor 100 may be implemented in hardware, firmware or software, or some combination of at least two of the same. The processor may also comprise memory storing machine-readable instructions executable for performing tasks. A processor acts upon information by manipulating, analyzing, modifying, converting or transmitting information for use by an executable procedure or an information device, and/or by routing the information to an output device. It should be noted that the functionality associated with any particular processor may be centralized or distributed, whether locally or remotely. In some embodiments, the processor 100 is included in a server 110. In other embodiments, the processor 100 is included in a computer 110. In other embodiments, the server 110 is a computer.

The system further includes one or more database(s) 102. The database(s) 102 may be local to the processor 100 and/or server or computer 110, or distributed and remote to the processor 100 and/or server or computer 110. For example, database 102 may be included on any hard disk or hard drive, an external storage device and/or portable media, such as a compact disc ("CD") or digital versatile disc ("DVD") accessible by a portable media device 120. The database 102 includes any number of directories and subdirectories including a plurality of electronic files accessible by the system. The files may be any electronic files of a particular type or many different types.

The system further includes a communication link 132 to link the processor 100 to a medical device 130 via software executing on the processor, on the medical device, or on both. For example, a user may use the medical device 130 (e.g., a scalpel) and the medical device 130 may be connected with the processor 100. In certain embodiments, the communication link 132 connects the medical device 130 to the processor 100 by wireless technology (such as WiFi, BLUETOOTH, ZigBee, optical or ultrasonic communication). In other embodiments, the medical device 130 is connected to the processor 100 by a wire or cable. In certain embodiments, the medical device 130 includes a sensor, an RFID tag, or a type of active or passive identifier that interacts with the computer.

When the medical device 130 is used and/or actuated, information is sent to the processor that the medical device is being used. In certain embodiments, the information is sent via data packets. In this way, the processor 100 is able to determine that the medical device 130 is being used, so that the subset of information on the display can be adjusted. In certain embodiments, the medical device may include an accelerometer or a device that detects movement of the medical device. In other embodiments, the medical device may include various controls, that when pressed, indicate to the processor that the medical device is being used. In certain embodiments, data signals are sent to the processor to indicate the medical device is being used. In certain embodiments, data signals are sent to the processor to indicate that a particular functionality of the medical device is being used, also including associated parameters for the functionality (e.g., pressure level of an insufflator, light intensity of a surgical light).

In FIG. 1, the processor 100 is linked to a display 140 by a communication link 134. In this manner, the processor 100 is linked to display 140 and is able to control the information on display 140. In certain embodiments, the communication link 134 connects display 140 to the processor 100 by wireless technology. In certain embodiments, the display 140 includes a sensor, an RFID tag, or a type of active or passive identifier that interacts with the computer. In other embodiments, the display 140 is connected to the processor 100 by a wire or cable.

By detecting that the user is using the medical device 130, the system is able to control the information displayed on the display 140. In certain embodiments, there are multiple displays, such that use of the medical device 130 can update the information displayed on each of the displays.

In FIG. 1, processor 100 also may be linked to additional medical device(s) 150 via communication link 136. Furthermore, the additional medical device(s) 150 are in communication with the processor 100, such that when the additional medical devices are in use and/or actuated, the subset of clinical information on the display is altered. In certain embodiments, additional medical device(s) 150 may include as many medical devices 150 as necessary to perform the medical or surgical procedure.

For example, in a surgical procedure, a laryngoscope may be used by a surgeon, and by using the laryngoscope, a certain subset of information may be present on a display. After inserting the laryngoscope into a patient, when the surgeon picks up a scalpel to perform a separate step in the medical procedure, the processor will communicate with the display to provide a different subset of information to the user, the subset of information being relevant to information surgeons need to know when making an incision in a patient, such as one made by a scalpel. In this manner, by detecting the use of various medical devices, the system is able to identify the phase of the surgical procedure, and to control the subset of information on the display. In certain embodiments, this clinical information is tailored to a specific step of the procedure, which is controlled at least in part by use of the medical device or more than one medical device.

In certain embodiments of the invention, the medical device may consist of medical devices such as a laryngoscope, endoscope, scalpel, intubation tube, stent, and/or other such medical devices that a user (such as a surgeon or nurse) may use during a medical procedure. In certain embodiments, the medical device includes input devices such as a keyboard, mouse, touch screen and/or a, footpedal.

In certain embodiments, the system includes software, the software executing on the processor 100 for controlling the subset of information displayed on the display. In certain embodiments, the processor is linked to the database 102, the database 102 being able to store rules to determine the subset of information to be provided by the use of each medical device.

In certain embodiments, a machine learning module 104 is shown in communication with the processor 100. The machine learning module 104 includes a set of rules derived from the analysis of current workflows, and provides rules that determine the subset of information that is shown on the display or momentarily hidden away. In this way a subset of information is displayed on the display 140, while information that is not relevant to the particular stage of the medical operation is not displayed on the display monitor. The machine learning module dynamically updates the rules by performing analysis of usage data.

In certain embodiments, the machine learning module 104 is dynamic, such that it has an engine (or uses the processor) that understands the subset of clinical information to display on the display 140, and is able to update the subset of clinical information on the display 140 based upon a request from a user. In certain embodiments, such a request is a voice command, a detected gesture, or an input command provided via a touchscreen, mouse or keyboard. The rules (or subset of clinical information to display) are not only updated when a specific request is issued by the user. The machine learning module may also collect usage statistic and events when a user overrides the default behavior provided by a rule or set of rules. Periodically, the rules are updated in such a way that if a consistent pattern of "overrides" is seen for a particular rule in a particular context (or by a particular user), then the rule is updated to reflect the new usage pattern in that context (or for that user). In certain embodiments, the rules are stored automatically within the database 102. In certain embodiments, the new usage pattern for that context (or for that user) is stored on the database 102.

In this manner, when a surgeon picks up a laryngoscope and the display 140 only displays a subset of clinical information (e.g. a subset regarding a patient's blood pressure) and the surgeon submits a command request to also show heart rate, then the machine learning module learns from the surgeon's command to have both blood pressure and the patient's heart rate shown on display 140. In this manner, the machine learning module 104 is able to learn from previous surgeries and is able to tailor the workflow of a medical procedure to a surgeon's individual preferences. The rules are updated only after a consistent usage pattern is observed over a certain period of time or number of procedures. For example, a consistent usage pattern may be three or more times in a row via the same surgeon. In certain embodiments, the rules have an associated risk level, so that rules having a high risk level are not automatically updated by the system. In certain embodiments, the risk level is expressed as a continuum between a minimum and a maximum value, so that rules with progressively higher risk level are only updated after a progressively larger set of usage data showing a consistent usage pattern is collected.

With regards to the override feature, the submission of the voice command to also show a patient's heart rate will trigger the system automatically refreshing the display to provide the patient's heart rate on the display.

In certain embodiments, a "workflow management module" is provided, which is based on the set of rules. In certain embodiments the workflow management module may be substituted for the machine learning module. In certain embodiments, the workflow management module maybe provided in addition to the machine learning module such that these modules are not exclusive of one another.

In certain embodiments, the system and method for managing workflow of a medical procedure is customizable to a surgeon's personal preferences or to industry standards, as often various surgical procedures have specific steps that are required when performing a standard surgery.

Figure 2:
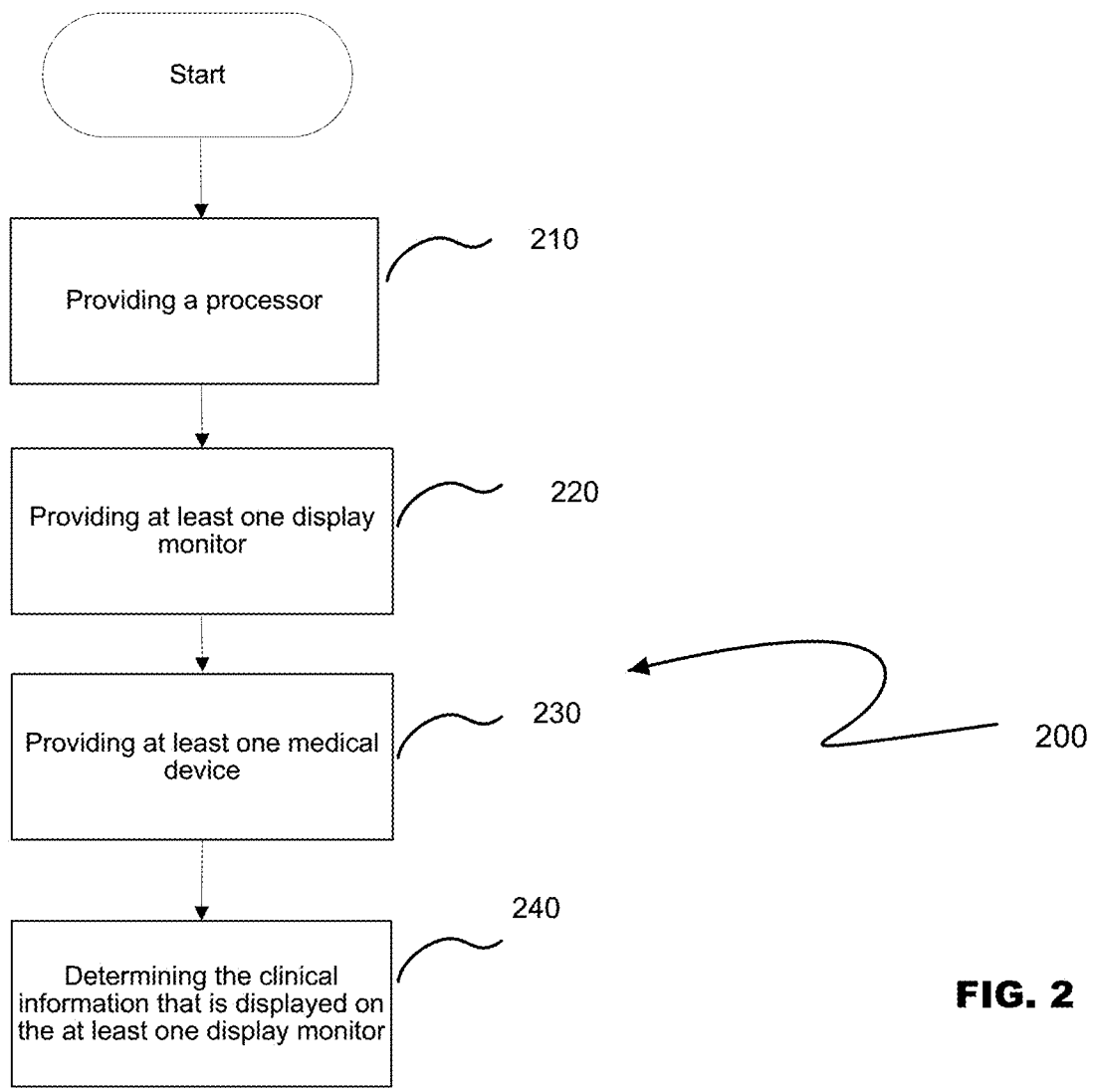
FIG. 2 is a flowchart of an embodiment of the present invention.

Referring to FIG. 2, a method 200 is provided for managing workflow of a medical procedure. Method 200 involves steps for providing a processor 210, providing at least one display monitor 220, providing at least one medical device 230 and determining the clinical information that is displayed on the at least one display monitor 240. In certain embodiments, method 200 is performed in an operating room.

In certain embodiments, the processor is able to process clinical information such as patient data or medical data. In certain embodiments, the processor is located within a computer or a server. In certain embodiments, the processor executes instructions that are stored on a memory or a computer medium.

In certain embodiments, the at least one display monitor is able to display the clinical information or a subset of clinical information. In certain embodiments, the at least one display monitor includes a graphical user interface and at least one dashboard, the at least one dashboard able to display clinical information.

In certain embodiments, the use of the at least one medical device in the medical procedure determines the clinical information that is displayed on the at least one display monitor.

In certain embodiments, the processor includes software, the software executing on the processor for controlling a subset of clinical information displayed on the at least one display monitor. In certain embodiments, the user of the at least one device at least partially determines a subset of clinical information that is displayed on the at least one display monitor by using voice commands or other type of input (keyboard, mouse, touch, gesture, physical buttons or switches on medical devices, etc.) to control the information on the display directly, or to override one or more of the rules triggered by the workflow management module.

Figure 3:
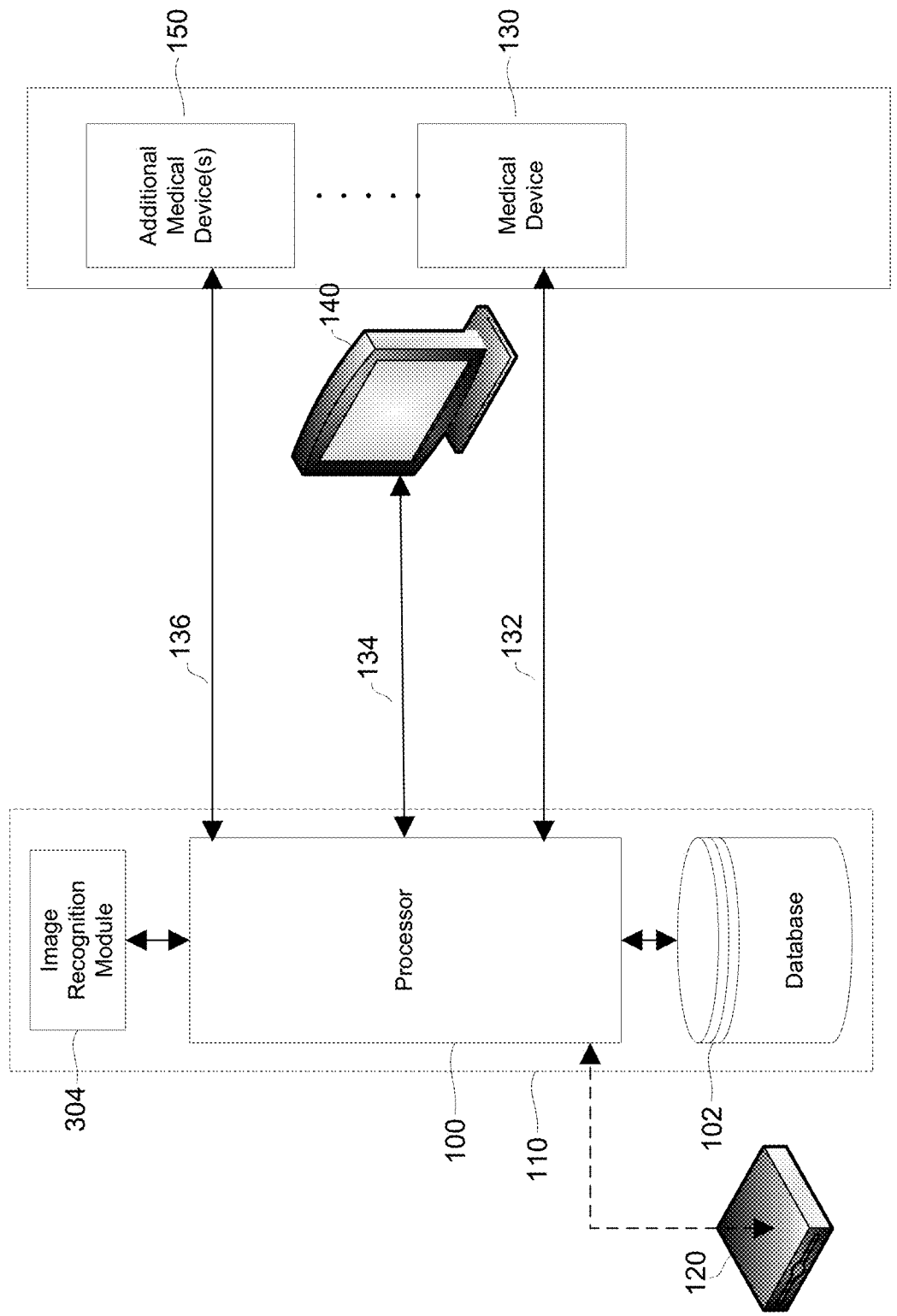
FIG. 3 is a schematic view of a surgical workflow support system of another embodiment of the present invention.

Referring to FIG. 3, FIG. 3 shows an exemplary system for managing workflow of a medical procedure in an operating room. FIG. 3 is similar to FIG. 1, but FIG. 3 includes an image recognition module 304 in place of machine learning module 104. Image recognition module 304 is able to detect a stage of the medical procedure to determine the subset of clinical information that is displayed on the at least one display monitor.

In this manner, image recognition module 304 is in communication with the processor 100 and determines the subset of clinical information that is displayed on the at least one display 140. More accurately, the image recognition module feeds the workflow management module which in turns determines the subset of clinical information to display.

In certain embodiments, the image recognition module 304 detects an approaching trocar port in the endoscopic camera image or detects the proximity of a medical device (such as an endoscope) to the trocar by using RFID or other type of sensors, or both. In certain embodiments, RFID and other type of sensors may be handled by a different module other than the image recognition module. The output of that module can be used as input to the image recognition module, for example to help it identify similar objects in the video image.

In this manner, the image recognition module is in communication with a workflow management module. The workflow management module is able to detect a stage of the medical procedure to determine the subset of clinical information that is displayed on the at least one display monitor.

The image recognition module, the machine learning module and the workflow management module are not mutually exclusive and can be part of the same system and methods of the claimed invention. Similarly, the voice recognition and gesture detection are both able to be used and implemented with a medical device of the same system and method.

In other examples, the workflow management module includes a speech recognition system. In this manner, the speech recognition system can detect a voice command, such as a surgeon asking a nurse to hand over a scalpel. In certain embodiments, the speech recognition system includes a microphone or device able to receive a voice command.

By having a voice command recognized, the workflow management system can understand that the scalpel is about to be used and can automatically update the clinical information on the at least one display that relates to a subset of information that is necessary when using the scalpel. This process can be done automatically as the voice command module is linked to a database having a set of rules. Once a rule in the database is recognized, then a function occurs whereby the clinical information on the at least one display is updated. In certain embodiments, the rules have an associated priority, so that the triggering of a lower priority rule does not override the effect(s) of a high priority rule.

Other objects of the present invention are achieved by various additional capabilities outlined below:

I. Reprogramming of Medical Devices

In certain embodiments of the invention, the system and method automatically reprograms the functionality of medical devices to control medical equipment. In these embodiments, the functionality of a control(s) on a medical device(s) is able to be reprogrammed such that the controls have different functionalities for different medical procedures as well as different stages of various medical procedures. In certain embodiments, the reprogramming of the devices occurs dynamically so that controls on the devices are reprogrammed to perform the most appropriate actions for the particular medical phase on the fly and during implementation of the medical procedure.

Figure 4:
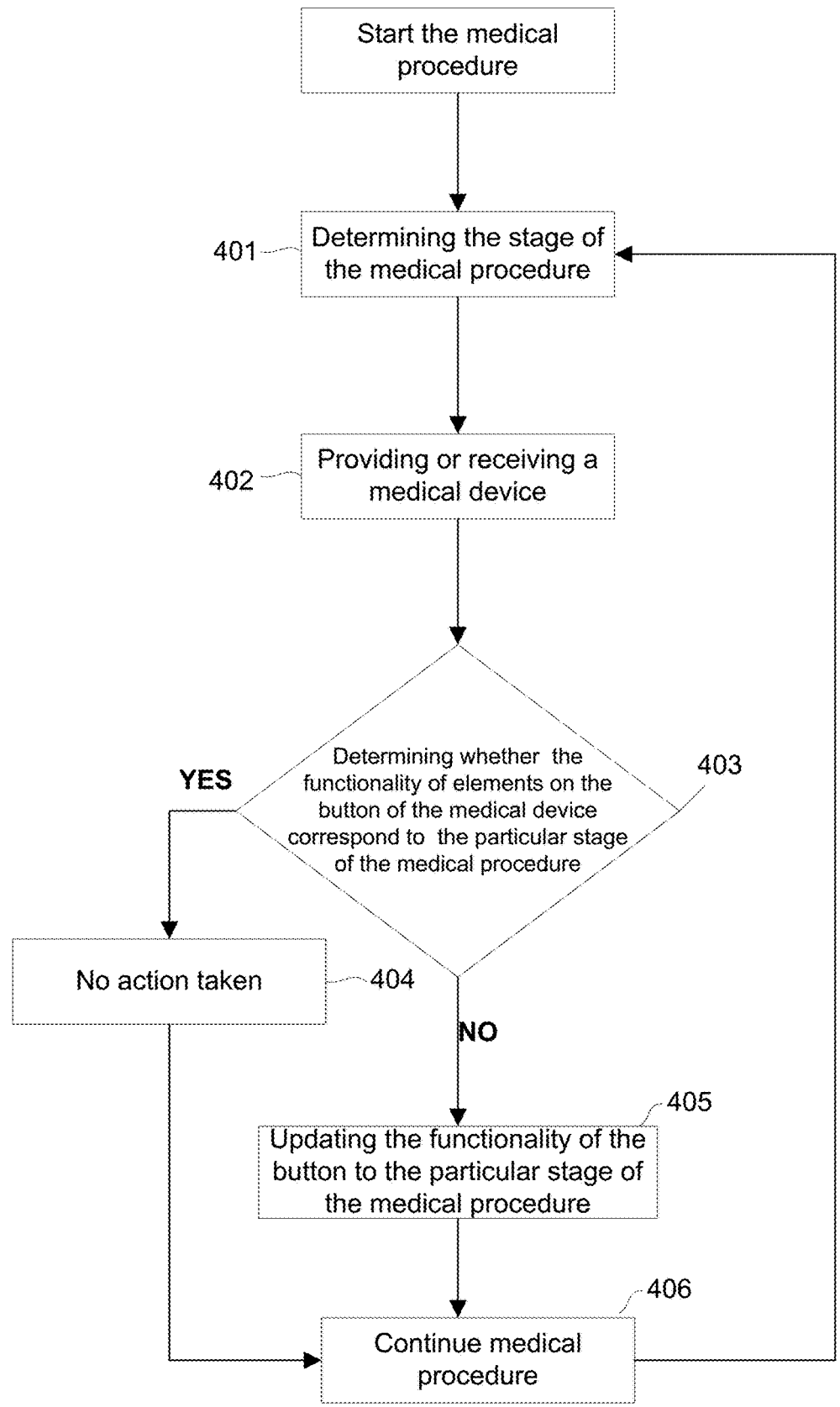
FIG. 4 is a flowchart of an embodiment of the present invention.

Referring to FIG. 4, a flowchart of an embodiment of the present invention is shown. In FIG. 4, the first step 401 involves determining the stage of the medical procedure. For example, the stage of the medical procedure may be an intubation step.

At 402, the method involves providing a medical device or receiving a medical device. At 403, the step involves determining whether the functionality of elements on the medical device correspond to the particular stage of the medical procedure. For example, during intubation, a laryngoscope may be used to intubate a patient. The laryngoscope may have various controls (such as buttons) that may turn on or off a light source within the laryngoscope and/or may turn on or off medical intubation gases, i.e the intubation function.

During the intubation phase, a single control may be used to control both the light source and the intubation function. The software executing on the processor may allow the single control to either control the light source or control the intubation function depending upon specific stage of the medical procedure. Accordingly, the control has more than one function and is dynamic, thus, reducing the amount of controls required and reducing the possibilities of a surgeon to make an error.

At 403, if the functionality of the control corresponds to the particular stage of the medical procedure, then no action is taken at 404. However, if the functionality of the control does not correspond to the particular stage of the medical procedure at 403, then at 405 the method involves updating the functionality of the control to the particular stage of the medical procedure. This process can be updated a plurality of times through the medical procedure as different elements on the medical devices can have different functionalities depending upon the particular stage of the medical procedure.

In certain embodiments, updating the functionality of the control on the medical device to the particular stage of the medical procedure is performed by software executing on the processor, which is in communication with the medical device through a communication link.

In certain embodiments, the at least one display is linked to the particular stage of the medical procedure such that a user is able to identify the particular functionality of the control at the particular stage of the medical procedure. For example, the display may include an icon indicating that a button on the laryngoscope is currently controlling the light source or the insufflation function.

In certain embodiments, the system reprograms input devices and employs heuristic learning to automatically and adaptively learn the preferred settings for each of the surgical phases.

In certain embodiments, the system repeats and continues the medical procedure as it goes back to step 401.

II. Machine Learning

In certain embodiments, the surgical workflow system is in communication with the medical devices in the IOR, and is thus aware of the type of procedure that is being performed (e.g., from the patient data, from a checklist module, or from a DICOM worklist). Since, in general, specific surgical procedures follow a more or less standardized set of steps or phases, it can be determined, either by a machine-learning module or by compiling a set of rules derived from the analysis of current workflows, the subset of clinical information that is shown.

Heuristic learning involves learning from previous surgical procedures, so that after a step in the medical procedure is overridden a few times, a rule is adapted that going forward, the step in the medical procedure is overridden. In certain embodiments, the heuristic learning is adapted to a user's preferences.

In certain embodiments, the system includes heuristic learning features, such that the system and the processor that executes the machine readable instructions learns from previous medical operations and updates the steps of the medical operation according to information learned from previous medical operations.

In certain embodiments, the machine learning module dynamically updates the rules by performing analysis of usage data.

Figure 5:
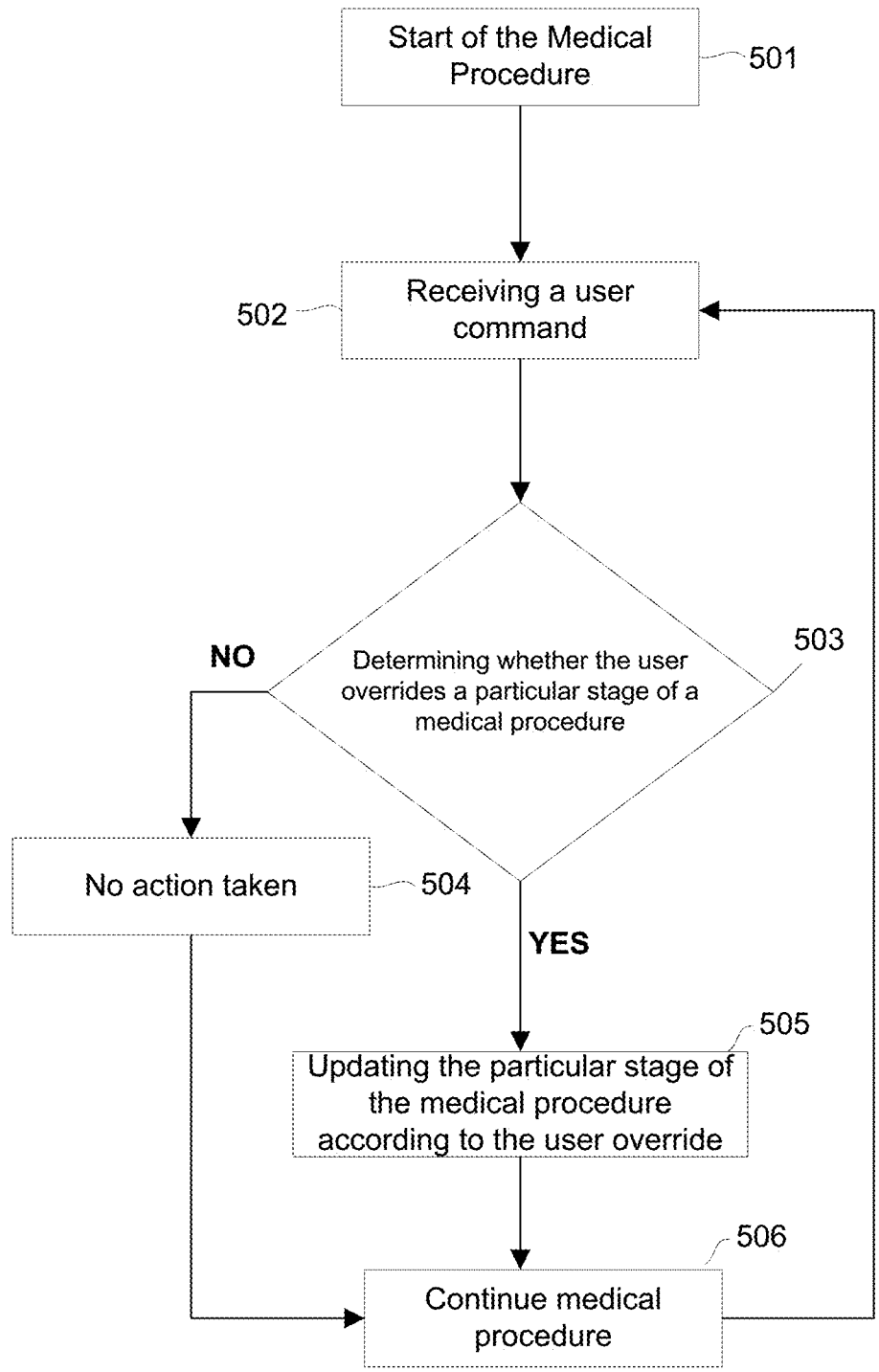
FIG. 5 is a flowchart of an embodiment of the present invention.

Referring to FIG. 5, a method for heuristic learning is shown. At 501, the medical procedure is started. At 502, the system receives a user command. In certain embodiments, the user command is a voice command, while in other embodiments, the user command is a command from a touchscreen or other such electronic device. In certain embodiments, the user command is given via a gesture.

At 503, the method involves determining whether the user command overrides a particular stage of a medical procedure. If not, then no action is taken. However, if yes, the system updates the particular stage of the medical procedure according to the user override 505. This allows the system to learn from previous operations, so that if the user command overrides a particular stage of a medical procedure, the particular stage of the medical procedure is updated. In certain embodiments, determining whether the user command overrides a particular stage of a medical procedure is achieved by interpreting a user command (e.g., a voice command, a gesture, or other input via touch screen, keyboard, mouse, footswitch, etc.) in the context of the particular stage. For example, if the system is set to display an X-Ray image when transitioning into a particular stage of the medical procedure, and the user immediately (or within a predetermined amount of time) issues a command to switch to an MRI image, then the system determines that the user command overrides one or more of the rules that triggered the display of the X-Ray image. In certain embodiments, the rules are updated only after a consistent usage pattern is observed over a certain period of time or number of procedures. At 506, the method continues the medical procedure. In certain embodiments, the system repeats and continues the medical procedure as it goes back to step 502.

In certain embodiments, the order of the particular stages can be stored in a memory, computer readable medium or a database. In certain embodiments, the system includes a series of rules, and the rules are determined according to each individual user and according to preferences of each individual user.

In certain embodiments, if a user override violates safety requirements and/or regulations, then a warning is given to the user.

In certain embodiments, the machine learning module is combined with the image recognition and voice recognition modules to further improve the capabilities of the surgical workflow support system. For example, if a new type of surgical instrument (e.g., a new scalpel) is developed after the surgical workflow support system is deployed, the image recognition module itself may not be able to recognize the new, never seen before, instrument. However, the system is able to correlate different types of information and instruct the image recognition module to learn the visual features of the new surgical system. For example, the surgical procedure requires use of a scalpel, the identified surgical phase indicates that incision is imminent, and the voice recognition module recognizes that the surgeon has asked the nurse to hand over the new scalpel. If the image recognition module does not positively identify the new scalpel, the system instructs it to construct a new visual model of the previously unseen scalpel. In other embodiments, the system applies algorithms similar to the one described above to learn new gestures and/or gesture commands.

In other embodiments, the system has an explicit "learning mode" which can be triggered by a user or by an administrator, typically as a maintenance procedure (and not during a surgery), whereby new medical instruments and/or gestures are "shown" to the system so they can be learned. For example, the image recognition module may have a user interface where a digital image or the live image of a new instrument is uploaded, together with a textual description of it. Then new rules can be added to the system to identify surgical phases associated with the use of the new surgical system. In other embodiments, the new rules are determined automatically by the machine learning module.

III. User Override

The surgical workflow support system also provides a simple mechanism (via GUI, touch panel, voice command, remote control, gesture recognition, etc.) to let the user override it at any time and, for example, to select different information to be displayed to the display monitor.

Figure 7:
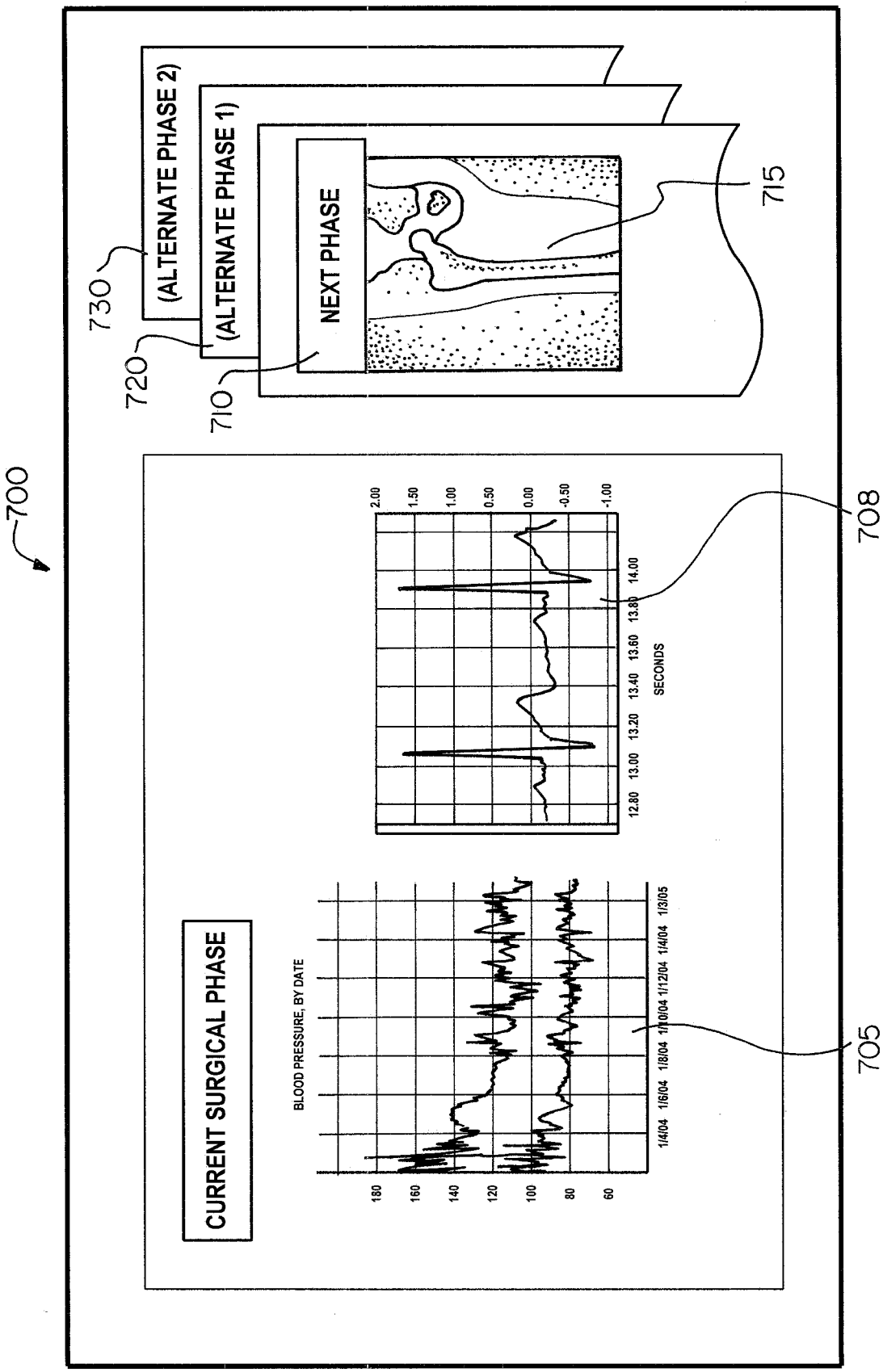
FIG. 7 is a graph of an override feature of an embodiment of the present invention.

In certain embodiments, the user override reprograms or reconfigures the medical procedure and in other embodiments, the user override simply alters the information the user wishes to have displayed on the display monitor. For example, as shown in FIG. 7, the display 700 displays information that is relevant to the current phase of the medical procedure. The next phase 710 for this type of procedure would require taking an X-Ray of the patient. However, if the current procedure is performed on a female patient and if there is a chance that the patient could be pregnant, than the surgeon may decide to override the default next phase 700 and chose an alternate diagnostic step or phase 720 or 730. The overriding can be performed by selecting the alternate phase on a touch screen, or by issuing a voice command and/or gesture or using some other input method.

In certain embodiments, the current surgical phase can display a blood pressure chart 705 by date and blood pressure chart 708 by time. In certain embodiments, the next phase 710 is shown displaying an image 715 and alternate phase 710 and alternate phase 720 are shown behind the next phase 710, such that an override will cause alternate phase 710 or alternate phase 720 to be displayed.

In certain embodiments, the user override reprograms or reconfigures certain functionalities of controls on medical devices, such that a command can cause a control on a medical device to have a different functionality moving forward during the surgical procedure and/or during subsequent surgical procedures.

IV. Reminder System

The workflow support system also provides reminders to a user or suggests that certain actions should be taken. As the surgical workflow system is in communication with the medical devices in the IOR, and is thus aware of the type of procedure that is being performed, and since, in general, specific surgical procedures follow a more or less standardized set of steps or phases, prompts are provided to remind or suggest that certain actions should be taken by a user.

In such a system, once a surgical step is completed, the system is able to remind the user what the next step is in the medical procedure through an audio message or visual message, such as a message displayed on a display. In such a system, the reminder messages help control the subset of information displayed on the at least one display. The workflow support system is also able to determine that a step of the medical procedure that was expected was not executed by the user, and may alert the user about the missed step. Thus, the ability to provide reminders to the user improves the workflow and/or the patient's safety during the medical procedure.

V. Operating Room Design

In certain embodiments of the invention, the invention decreases clutter in a surgical operating room. In certain embodiments, the workflow support system automatically detects and identifies individual surgical phases and/or tasks.

In certain embodiments, the system allows to greatly simplify the man-machine interface by eliminating some of the multitude of similar control devices (e.g., camera head buttons, footswitches, etc.). In certain embodiments, the medical devices in the operating room have several programmable controls, such as buttons. The functionality currently provided by several buttons can be dynamically and intelligently assigned to only one or two buttons to reduce the clutter and increase overall situational awareness control of the operating room. The workflow support system shows the function assigned to each programmable control on one or more of the displays. In this manner, the user understands the functionality of each control during each stage of the medical procedure.

In certain embodiments, the software executing on the processor is able to automatically navigate the IOR through the various settings that are required for each phase or task. For example, the system detects when transitioning from minimally invasive surgery to open surgery and the system configures the instruments for an open surgery by reconfiguring the buttons on the medical devices for the open surgery.

In certain embodiments, use of the medical devices provides input to the workflow support system, which in turn controls the data displayed on the one or more display monitors.

In certain embodiments, a medical device (e.g. camera head with buttons) performs different functions depending upon the phase of the medical procedure. The controls on the medical device switch functionality based upon the step of the medical procedure.

Other embodiments of the operating room design include providing various medical devices in the operating room including a camera control unit ("CCU"), various cameras and camera units in communication with the CCU and the processor. In certain embodiments, use of the cameras can control the clinical information provided to the display.

In certain embodiments, the at least one medical device sends data packets to the processor to indicate that the medical device is in use. In certain embodiments, the system uses data from medical devices to identify steps and/or phases of the surgery. For example, once a valve to pump gas is actuated in an insufflation unit, the system knows that insufflation will begin shortly and the relevant data is displayed on the display pertaining to insufflation in a patient.

In certain embodiments, the surgical workflow support system is in communication with the devices in the OR, and can thus send appropriate instructions to the CCU to program the functions associated to the camera buttons.

In certain embodiments, the system includes artificial intelligence. In certain embodiments, the artificial intelligence includes statistical methods and algorithms so that the machine learning module and workflow management system are able to learn and interact to optimize the medical procedure. In certain embodiments, the workflow management system is triggered when at least one member of the surgical team logs in into the system, or when the patient/procedure data is downloaded from a DICOM server, or based on the IOR schedule.

VI. Computer System

Figure 6:
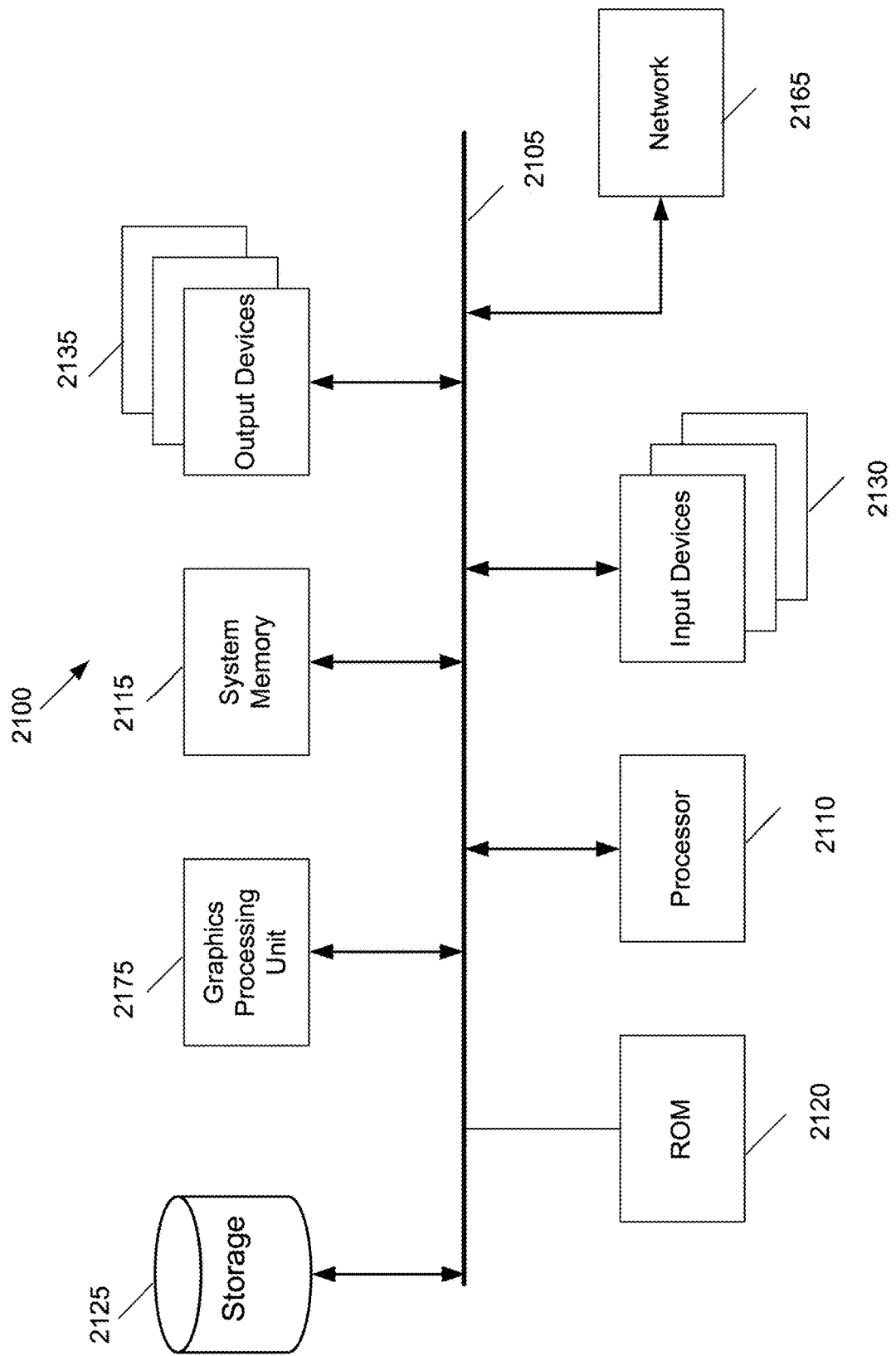
FIG. 6 is a schematic of a computer system that supports the embodiments shown in FIG. 1.

FIG. 6 conceptually illustrates a computer system with which some embodiments of the invention are implemented. The computer system 2100 includes a bus 2105, a processor 2110, a system memory 2115, a read-only memory 2120, a permanent storage device 2125, input devices 2130, and output devices 2135. In some embodiments, the computer system also includes a graphic processing unit (GPU) 2175.

The bus 2105 collectively represents all system, peripheral, and chipset buses that support communication among internal devices of the computer system 2100. For instance, the bus 2105 communicatively connects the processor 2110 with the read-only memory 2120, the system memory 2115, and the permanent storage device 2125.

From these various memory units, the processor 2110 (also referred to as central processing unit or CPU) retrieves instructions to execute and data to process in order to execute the processes of the invention. The read-only-memory (ROM) 2120 stores static data and instructions that are needed by the processor 2110 and other modules of the computer system.

The permanent storage device 2125, on the other hand, is a read-and-write memory device. This device is a non-volatile memory unit that stores instruction and data even when the computer system 2100 is off. Some embodiments of the invention use a mass-storage device (such as a magnetic or optical disk and its corresponding disk drive) as the permanent storage device 2125. The permanent storage device 2125 may be a fully solid-state storage, a conventional "spinning magnetic pallet" storage (i.e. hard-drive), or combinations thereof.

Other embodiments may use a removable storage device (such as a USB flash drive or SD Memory Card) as a temporary storage or as the permanent storage device 2125.

Like the permanent storage device 2125, the system memory 2115 is a read and write memory device. However, unlike storage device 2125, the system memory is a volatile read-and-write memory, such as a random access memory.

The system memory stores at least some of the instructions and data that the processor needs at runtime.

Instructions and/or data needed to perform processes of some embodiments are stored in the system memory 2115, the permanent storage device 2125, the read-only memory 2120, or any combination of the three. For example, the various memory units may contain instructions for processing multimedia items in accordance with some embodiments. From these various memory units, the processor 2110 retrieves instructions to execute and data to process in order to execute the processes of some embodiments.

The bus 2105 also connects to the input and output devices 2130 and 2135. The input devices enable the user to communicate information and select commands to the computer system. The input devices 2130 include alphanumeric keyboards, touch panels, and cursor controllers. The input devices 2130 also include scanners through which an image can be input to the computer system. The output devices 2135 display images generated by the computer system. The output devices may include printers, pen plotters, laser printers, ink-jet plotters, film recorders, and display devices, such as cathode ray tubes (CRT), liquid crystal displays (LCD), or electroluminescent displays.

As shown in FIG. 6, bus 2105 also couples computer 2100 to a network 2165 through a network adapter (not shown). In this manner, the computer can be a part of a network of computers (such as a local area network ("LAN"), a wide area network ("WAN"), or an Intranet) or a network of networks (such as the Internet). Finally, as shown in FIG. 6, the computer system in some embodiments also optionally includes a graphics processing unit (GPU) 2175. A GPU (also referred to as a visual processing unit or a display processor) is a dedicated graphics rendering device which is very efficient in manipulating and displaying computer graphics. The GPU can be included in a video card (not shown) or can be integrated into the mother board of the computer system along with the processor 2110. Also, the computer system 2100 may be used as a personal computer, a workstation, a game console, or the like. Any or all of the components of computer system 2100 may be used in conjunction with the invention. However, one of ordinary skill in the art will appreciate that any other system configuration may also be used in conjunction with the invention.

Example 1

Laparoscopy Procedure

In certain embodiments, the system is used for a laparoscopy procedure. During a laparoscopy, as the phase detector identifies that an endoscope is about to be inserted into a trocar (for example, an accelerometer sensor on the endoscope detects initial movement, or the image recognition module recognizes that the endoscope is approaching the trocar), the workflow support system reminds the surgeon to white-balance the camera, while at the same time programming a camera head button to perform the white-balance function. If the white-balance function has already been activated by the user, then the system will skip such reminder.

Then, as the endoscope is inserted (and the insertion is detected as a phase or task), the same camera head button is reprogrammed to control the intensity of the light source or control the insufflators and adjust insufflation gas pressure. And finally, during the actual surgical procedure, the camera head button is again reprogrammed to take pictures and videos of the surgical image.

In other embodiments of a laparoscopy procedure, before the start of the actual procedure, while the patient is prepared for intubation, one or more displays show his/her vital signs. When intubation actually starts, one or more displays are switched to the intubation camera. In this example, the displays are adjusted based upon the intubation and the use of the medical intubation device. Accordingly, the one or more displays automatically present the relevant information to an anesthesiologist that has to deal with information relevant for intubation.

In certain examples, the surgical workflow support system starts in an idle state. Then, when a patient is brought into the IOR and hooked up to the various monitors (e.g. monitoring hearth rate, blood pressure, etc.) the system transitions to a pre-surgery phase. Such transition does not need any specific operator input, as it is performed automatically when the vital signs monitors start reading some actual values. The vital signs of the patient are then displayed on one or more monitors. A transition to the intubation phase is triggered when a number of conditions are met. Specifically: the current phase is pre-surgery, the type of procedure requires intubation, the intubation camera and associated light source are turned on (if not already on), and an image processing software that is fed the intubation camera image detects at least some motion in the image. The image processor may also detect when the endoscope is approaching the patient's mouth by using an image recognition algorithm.

When the above conditions are met, one or more of the displays are switched showing information from the intubation camera by sending appropriate control commands to a video routing module.

Similarly, a transition to a "post-intubation" phase is triggered when: the current phase is intubation, the anesthesia workstation is pumping gas, the intubation camera is removed (again, detected by the image processor) and/or turned off In certain embodiments, a method is provided for managing workflow of an intubation procedure in an operating room, the method comprising: preparing a patient for intubation by connecting a patient to at least one monitor; displaying the vital signs of the patient automatically on at least one display monitor prior to intubation of the patient; powering on an intubation camera; powering on an associated light source; connecting the intubation camera to a control unit, the control unit having image processing software that detects at least some motion in an image provided by the intubation camera; switching at least one display to the intubation camera by sending appropriate control commands to a video routing module; and controlling the steps of the medical procedure via an intubation unit, wherein the use of the intubation unit determines the subset of clinical information that is displayed on the at least one display monitor.

Example 2

Providing Relevant Information on the Display

Another embodiment of the present invention involves providing relevant information on the display. The information (e.g., patient information, X-Rays, CT scans, MRI scans, status of devices, etc.) provided to the surgical team is organized so that each type of information is shown only when it is needed: the patient name, case number, type of procedure, etc., are displayed when the surgical team checks in, the X-Rays are shown while the patient is positioned for the procedure, the MRI scans are shown prior to incision. Once again, the ability to provide only the right information at the right time allows to both reduce the information overload for the whole surgical team and to reduce clutter in the IOR by rendering one or more displays no longer necessary.

In certain embodiments, the information is collected and analyzed from all connected medical devices. In laparoscopic surgery, important data is provided by an HF generator, an insufflator, a pump, a light source, a surgical light and the OR table for example. The above collected information will be used to identify the current surgical phase for a specific type of surgery.

In certain embodiments, the actual phase detection technology can also be improved and made more accurate by considering the parameters and data provided by the connected medical devices. For example, when using a light source, the transition from a low to a high level of light intensity indicates that the endoscope is about to be inserted in the body. In this manner, clinical information related to a patient's body is displayed on the at least one display and the system knows that the particular stage of the surgery where the endoscope is inserted into the body has commenced.

In other examples, the light intensity can be combined with the pressure level of an insufflator to provide more reliable phase detection. Similarly, the power level of an HF device indicates when cautery is in progress, allowing to identify the related procedural step.

Note that increasingly fine grained steps and/or surgical phases can be identified by combining information from several devices. For example, when both a cautery and a suction device are active, the system may infer that the surgeon is removing tissue, whereas the use of the cautery device alone may indicate the sealing of a small blood vessel.

Thus, use of the at least one medical device or even two or more medical devices determines the subset of clinical information that is displayed on the at least one display monitor. This allows the relevant information to be displayed on the at least one display monitor automatically.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A surgical control system for a multi-stage medical procedure having a plurality of stages including at least a first stage and a second stage, each of the plurality of stages requiring a medical procedure different from each other, comprising:
    an endoscope, the endoscope including camera head having a camera head button for actuating a camera function from a plurality of camera functions, the camera head button actuated by a physical touch, the camera function corresponding to an output of the endoscope;
    a database storing clinical information;
    a display monitor;
    a processor executing software written on memory hardware, the memory hardware storing instructions that when executed cause the processor to perform operations comprising:
    determining a stage of the multi-stage medical procedure based at least partially on a use of the endoscope;
    determining a subset of the clinical information based on the stage of the medical procedure;
    displaying the determined subset of clinical information on the display monitor; and
    reprogramming the camera head button during different stages of the medical procedure, wherein in the first stage the camera head button is programmed to actuate the endoscope to generate a first output corresponding to the camera function of the first stage and in the second stage the camera head button is reprogrammed to actuate the endoscope to generate a second output corresponding to the camera function of the second stage, the first output being different than the second output.

2. The system of claim 1, wherein a different subset of the clinical information is displayed on the display monitor for each stage of the medical procedure.

3. The system of claim 1, wherein a physical movement of the endoscope at least partially controls the subset of clinical information displayed on the display monitor.

4. The system of claim 1, wherein the endoscope includes control parameters, and changes to the control parameters at least partially controls the subset of clinical information displayed on the display monitor.

5. The system of claim 1, wherein the endoscope includes a sensor, an RFID tag, or a type of active or passive identifier that interacts with the processor.

6. The system of claim 1, further including a machine learning module communicatively coupled to the processor.

7. The system of claim 6, wherein the machine learning module includes rules that adjust steps of the medical procedure based at least partially on use of the endoscope.

8. The system of claim 7, wherein the machine learning module updates the rules after receiving commands via speech recognition and/or gesture control and/or an input device.

9. The system of claim 7, wherein the rules have an associated risk level, so that rules having a high risk level are not automatically updated.

10. The system of claim 9, wherein the risk level is expressed as a continuum between a minimum and a maximum value, so that rules with high risk level are only updated after a large set of usage data showing a consistent usage pattern is collected.

11. The system of claim 1, further comprising image recognition module communicatively coupled to the processor.

12. The system of claim 11, wherein the image recognition module at least partially uses image recognition algorithms to identify features in signals provided by the endoscope to determine the subset of clinical information to be displayed.

13. The system of claim 11, wherein the image recognition module is augmented by speech recognition and/or gesture control.

14. The system of claim 11, wherein the image recognition module learns visual features of the endoscope and/or gestures.

15. The system of claim 1, further including endoscope parameters to at least partially determine a stage of the medical procedure.

16. The system of claim 15, wherein information provided by the endoscope is used to identify sub-steps of the medical procedure.

17. The system of claim 1, wherein the input is a speech recognition module and/or gesture control module.

18. The system of claim 1, wherein the processor includes an override that allows a user to control the subset of clinical information displayed on the display monitor.

19. The system of claim 1, further comprising software executing on the processor that provides reminders to suggest steps be taken by a user during the medical procedure.

20. The system of claim 1, further comprising software executing on the processor that provides audible warnings to a user.

21. The system of claim 1, wherein the medical procedure is a transplant surgery.

22. The system of claim 1, wherein progress of the medical procedure is monitored.

23. The system of claim 22, wherein updates on progress of the medical procedure are provided through the display monitor.

24. The system of claim 1, wherein the clinical information is divided into subsets according to a role of an intended recipient.

25. The system of claim 24, further including a second display monitor, wherein the display monitor displays a subset of information relevant for a first intended recipient, and the second display monitor displays a subset of information relevant for a second intended recipient.

26. The system of claim 1, wherein the input includes at least one of a camera head button and a footswitch.

27. The system of claim 1, wherein during one stage of the medical procedure the controller when operated controls intubation and during another stage of the medical procedure the controller is reprogrammed so that when operated it controls a cutting mechanism.

28. The system of claim 1, wherein the plurality of camera functions includes adjusting a white-balance function, taking a picture, taking a video, adjusting a light intensity, and turning on or off a light source.

29. A method for using a surgical control system for a multi-stage medical procedure having a plurality of stages including at least a first stage and a second stage, each of the plurality of stages requiring a medical procedure different from each other, the method comprising:
    providing an endoscope, the endoscope including a camera head having a camera head button for actuating a camera function from a plurality of camera functions, the camera head button actuated by a physical touch, the camera function corresponding to an output of the endoscope;
    providing a database storing clinical information;
    providing a display monitor;
    determining, with a processor, a stage of the multi-stage medical procedure based at least partially on a use of the endoscope;
    determining, with the processor, a subset of the clinical information for display on the display monitor based on the stage of the medical procedure;
    displaying the subset of the clinical information on the display;
    reprogramming the camera head button during different stages of the medical procedure, wherein in the first stage the camera head button is programmed to actuate the endoscope to generate a first output corresponding to the camera function of the first stage and in the second stage the camera head button is reprogrammed to actuate a the endoscope to generate a second output corresponding to the camera function of the second stage, the first output being different than the second output; and
    using the input to control the camera function of the endoscope.

30. The method of claim 29, wherein the endoscope includes a sensor, an RFID tag, or a type of active or passive identifier that interacts with the processor.

31. The method of claim 29, wherein the processor includes an override that allows a user to control the subset of clinical information displayed on the display monitor.

32. The method of claim 31, wherein the override is based at least in part upon a voice command, a gesture, or an input command.

33. The method of claim 29, wherein the input is a speech recognition module and/or gesture control module.

34. The method of claim 29, further comprising software executing on the processor that provides reminders to suggest steps be taken by a user during the medical procedure.

35. The method of claim 29, wherein the plurality of camera functions includes adjusting a white-balance function, taking a picture, taking a video, adjusting a light intensity, and turning on or off a light source.

36. A surgical control system for a multi-stage medical procedure having a plurality of stages including a first stage and a second stage, each of the stages requiring a medical procedure different from each other, the system comprising:
    an endoscope, the endoscope including an input for actuating a camera function from a plurality of camera functions, the camera function corresponding to an output of the endoscope;
    a database storing clinical information;
    a display monitor;
    an image recognition module configured to capture images;
    a processor executing software written on memory hardware, the memory hardware storing instructions that when executed cause the processor to perform operations comprising:
    processing the images captured by the image recognition module to determine a surgical scene:
    determining a stage of the multi-stage medical procedure based at least partially on a use of the endoscope, the surgical scene and a position of the endoscope with respect to the surgical scene;
    determining a subset of the clinical information based on the stage of the medical procedure;
    displaying the determined subset of clinical information of the display monitor; and
    reprogramming the input during different stages of the medical procedure, wherein in the first stage the input is programmed to actuate the endoscope to generate a first output corresponding to the camera function of the first stage and in the second stage the input is reprogrammed to actuate the endoscope to generate a second output corresponding to the camera function of the second stage, wherein the first output is different than the second output.

37. The system of claim 36, wherein the endoscope interacts with the image recognition module via a sensor, an RFID tag, or a type of active or passive identifier.

38. The system of claim 36, further including a software executing on the processor that provides reminders to suggest steps to be taken by a user during the medical procedure.

39. The system of claim 36, wherein the input is a speech recognition module and/or gesture control module.

40. The system of claim 36, wherein the image recognition module is augmented by speech recognition and/or gesture control and/or an input device.

41. The system of claim 36, wherein the plurality of camera functions includes adjusting a white-balance function, taking a picture, taking a video, adjusting a light intensity, and turning on or off a light source.

42. The system of claim 36, wherein the first stage of the medical procedure is the endoscope approaching a trocar, and the second stage of the medical procedure is the endoscope inserted into the trocar.

* * * * *